(12) United States Patent
Zhang (10) Patent No.: US 7,150,760 B2
(45) Date of Patent: Dec. 19, 2006

(54) ACCOMMODATIVE INTRAOCULAR LENS SYSTEM

(75) Inventor: Xiaoxiao Zhang, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 435 days.

(21) Appl. No.: 10/805,921

(22) Filed: Mar. 22, 2004

(65) Prior Publication Data

US 2005/0209692 A1 Sep. 22, 2005

(51) Int. Cl.
*A61F 2/16* (2006.01)

(52) U.S. Cl. .................. 623/6.37; 623/6.39

(58) Field of Classification Search ........... 623/6.11, 623/6.27, 6.32–6.4, 6.43
See application file for complete search history.

(56) References Cited

U.S. PATENT DOCUMENTS

| 5,275,623 | A | 1/1994 | Sarfarazi |
| 5,476,514 | A | 12/1995 | Cumming |
| 5,496,366 | A | 3/1996 | Cumming |
| 5,674,282 | A | 10/1997 | Cumming |
| 6,197,059 | B1 | 3/2001 | Cumming |
| 6,241,777 | B1 | 6/2001 | Kellan |
| 6,261,321 | B1 | 7/2001 | Kellan |
| 6,302,911 | B1 | 10/2001 | Hanna |
| 2002/0107568 | A1 | 8/2002 | Zadno-Azizi et al. |
| 2004/0039446 | A1 | 2/2004 | McNicholas |

FOREIGN PATENT DOCUMENTS

| WO | WO 01/34067 | 11/1999 |
| WO | WO 00/66037 | 11/2000 |
| WO | WO 03/059196 | 7/2003 |
| WO | WO 03/059208 | 7/2003 |

OTHER PUBLICATIONS

"A dual optic accommodating foldable intraocular lens" British Journal of Ophthalmology 2003; 87: 1083-1085.

*Primary Examiner*—Eduardo C Robert
*Assistant Examiner*—William H Matthews
(74) *Attorney, Agent, or Firm*—Jeffrey S. Schira (57) ABSTRACT

A two optic accommodative lens system. The first lens in the system is fixed in the anterior chamber of an eye. The second lens in the system includes a non-circular ring with radial dimensions that are different in at least two meridians and implanted in the posterior chamber of an eye within the capsular bag. The radial dimension of vertical meridian of the lens approximates the natural diameter of the capsular bag. The optic of the second lens is connected to the ring at the vertical meridian by two or more of haptics. The radial dimension of horizontal meridian of the second lens is slightly larger than the natural diameter of the capsular bag.

11 Claims, 13 Drawing Sheets

ACCOMMODATIVE INTRAOCULAR LENS SYSTEM

BACKGROUND OF THE INVENTION

This invention relates generally to the field of intraocular lenses (IOL) and, more particularly, to accommodative IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In the way, the natural lens can be focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior to the present invention, when a cataract or other disease required the removal of the natural lens and replacement with an artificial IOL, the IOL was a monofocal lens, requiring that the patient use a pair of spectacles or contact lenses for near vision. Advanced Medical Optics has been selling an bifocal IOL, the Array lens, for several years, but due to quality of issues, this lens has not been widely accepted.

Several designs for accommodative IOLs are being studied. For example, several designs manufactured by C&C Vision are currently undergoing clinical trials. See U.S. Pat. Nos. 6,197,059, 5,674,282, 5,496,366 and 5,476,514 (Cumming), the entire contents of which being incorporated herein by reference. The lens described in these patents is a single optic lens having flexible haptics that allows the optic to move forward and backward in reaction to movement of the ciliary muscle. A similar designs are described in U.S. Pat. No. 6,302,911 B1 (Hanna), U.S. Pat. No. 6,261,321 B1 and U.S. Pat. No. 6,241,777 B1 (both to Kellan), the entire contents of which being incorporated herein by reference. The amount of movement of the optic in these single-lens systems, however, may be insufficient to allow for a useful range of accommodation. In addition, as described in U.S. Pat. Nos. 6,197,059, 5,674,282, 5,496,366 and 5,476,514, the eye must be paralyzed for one to two weeks in order for capsular fibrosis to entrap the lens that thereby provide for a rigid association between the lens and the capsular bag. In addition, the commercial models of these lenses are made from a hydrogel or silicone material. Such materials are not inherently resistive to the formation of posterior capsule opacification ("PCO"). The only treatment for PCO is a capsulotomy using a Nd:YAG laser that vaporizes a portion of the posterior capsule. Such destruction of the posterior capsule may destroy the mechanism of accommodation of these lenses.

There have been some attempts to make a two-optic accommodative lens system. For example, U.S. Pat. No. 5,275,623 (Sarfarazi), WIPO Publication No. 00/66037 (Glick, et al.) and WO 01/34067 A1 (Bandhauer, et al), the entire contents of which being incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the capsular bag, and none of these references disclose a mechanism for ensuring that there is a tight connection between the capsular bag and the lens system. In addition, none of these lenses designs have addressed the problem with PCO noted above.

Therefore, a need continues to exist for a safe and stable accommodative intraocular lens that provides accommodation over a broad and useful range.

BRIEF SUMMARY OF THE INVENTION

The present invention improves upon the prior art by providing a two optic accommodative lens system. The first lens in the system is fixed in the anterior chamber of an eye. The second lens in the system includes a non-circular ring with radial dimensions that are different in at least two meridians and implanted in the posterior chamber of an eye within the capsular bag. The radial dimension of vertical meridian of the lens approximates the natural diameter of the capsular bag. The optic of the second lens is connected to the ring at the vertical meridian by two or more of haptics. The radial dimension of horizontal meridian of the second lens is slightly larger than the natural diameter of the capsular bag.

Accordingly, one objective of the present invention is to provide a safe and biocompatible intraocular lens system.

Another objective of the present invention is to provide a safe and biocompatible intraocular lens system that is easily implanted in the posterior chamber.

Still another objective of the present invention is to provide a safe and biocompatible intraocular lens system that is stable in the posterior chamber.

Still another objective of the present invention is to provide a safe and biocompatible accommodative lens system.

These and other advantages and objectives of the present invention will become apparent from the detailed description and claims that follow.

DETAILED DESCRIPTION OF THE INVENTION

Figure 1:
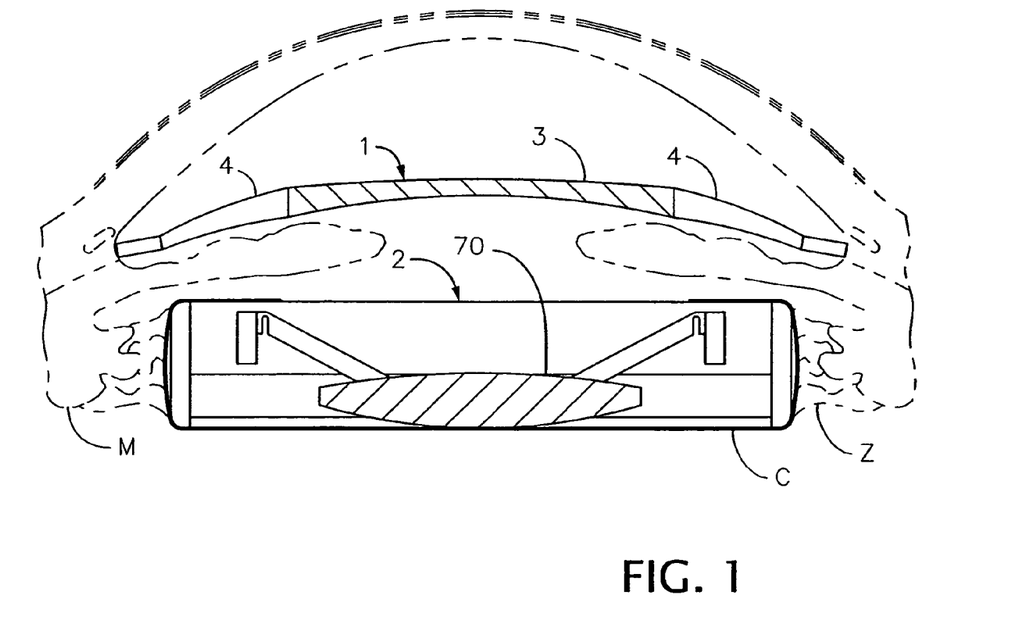
FIG. 1 is an enlarged cross-sectional view showing the lens system of the present invention implanted in an eye and with the second lens of the system in the far focused position.
Figure 2:
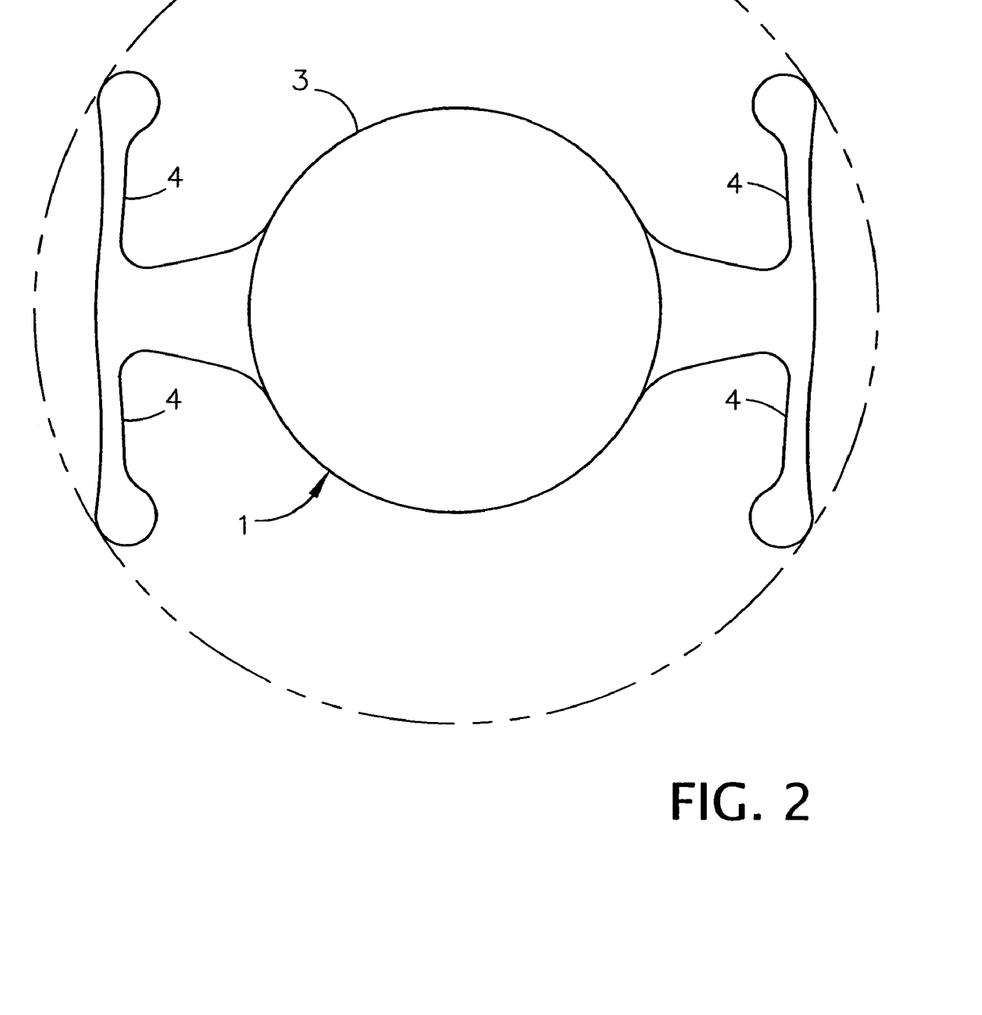
FIG. 2 is an enlarged plan view of the first lens of the lens system of the present invention.

As best seen in FIG. 1, the present invention comprises two lens assemblies, fixed lens assembly 1 positioned in the anterior chamber of an eye and moving lens assembly 2, which is positioned in an evacuated capsule C of the eye. Fixed lens assembly 1 comprises fixed lens 3 secured by two or more haptics 4. FIG. 2 shows a top view of fixed lens assembly 1. Lens assemblies 1 and 2 and lenses 3 and 70 may be made from any suitable material such as a thermoplastic, a silicone, a hydrogel or a soft acrylic and contain any desired additives, such as ultraviolet or blue light blocking chromophores. Lenses 3 and 70 may have any suitable design, such aspheric, toric, pseudoaccommodative or multifocal. Those skilled in the art will recognize that lens assemblies 1 and 2 need not be implanted at the same time. For example, lens assembly 2 may be implanted in an eye and the eye allowed to recover from the surgical trauma. After waiting such a healing period, bioptric and other physiological measurements may be made sufficient to calculate an accurate prescription for lens assembly 1, at which time lens assembly 1 may be implanted.

FIG. 1 shows moving lens assembly 2 in a far focusing position, where moving lens 70 is at a posterior location, which is the farthest from fixed lens 3. Now referring to FIG. 3, moving lens assembly 2 is shown in a near focusing position, where moving lens 70 is at an anterior location, which is nearest fixed lens 3.

Figure 3:
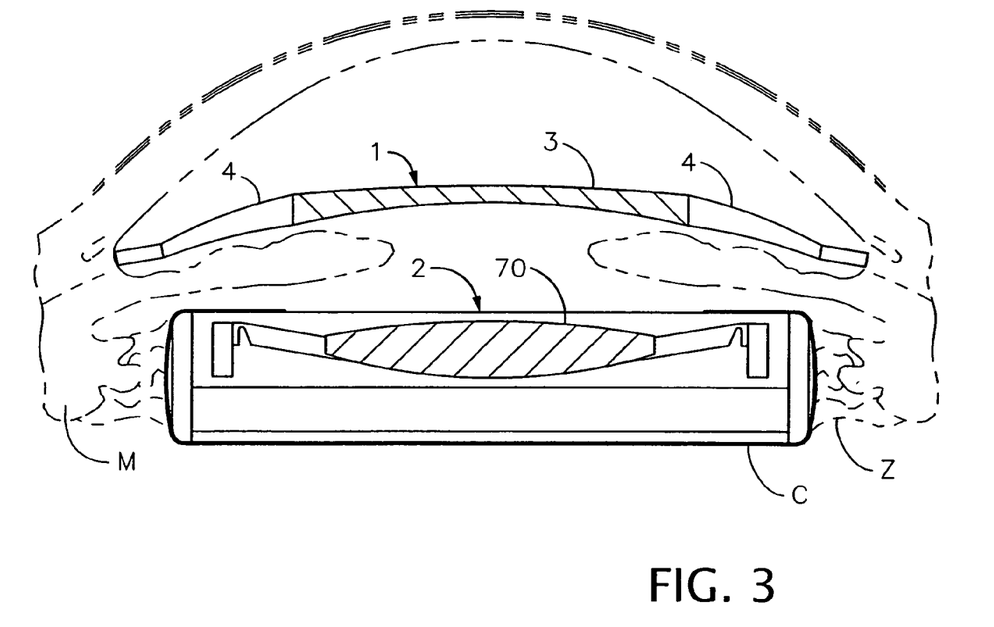
FIG. 3 is an enlarged cross-sectional view showing the lens system of the present invention implanted in an eye and with the second lens of the system in the near focused position.

Taken together, fixed lens 3, and moving lens 70, form an optical system, whose focus changes with a corresponding change in the distance between the lenses 3 and 70. The actuation of moving lens assembly 2 will be disclosed as comprising a compound action, powered by the ciliary muscle M of the eye.

Figure 4:
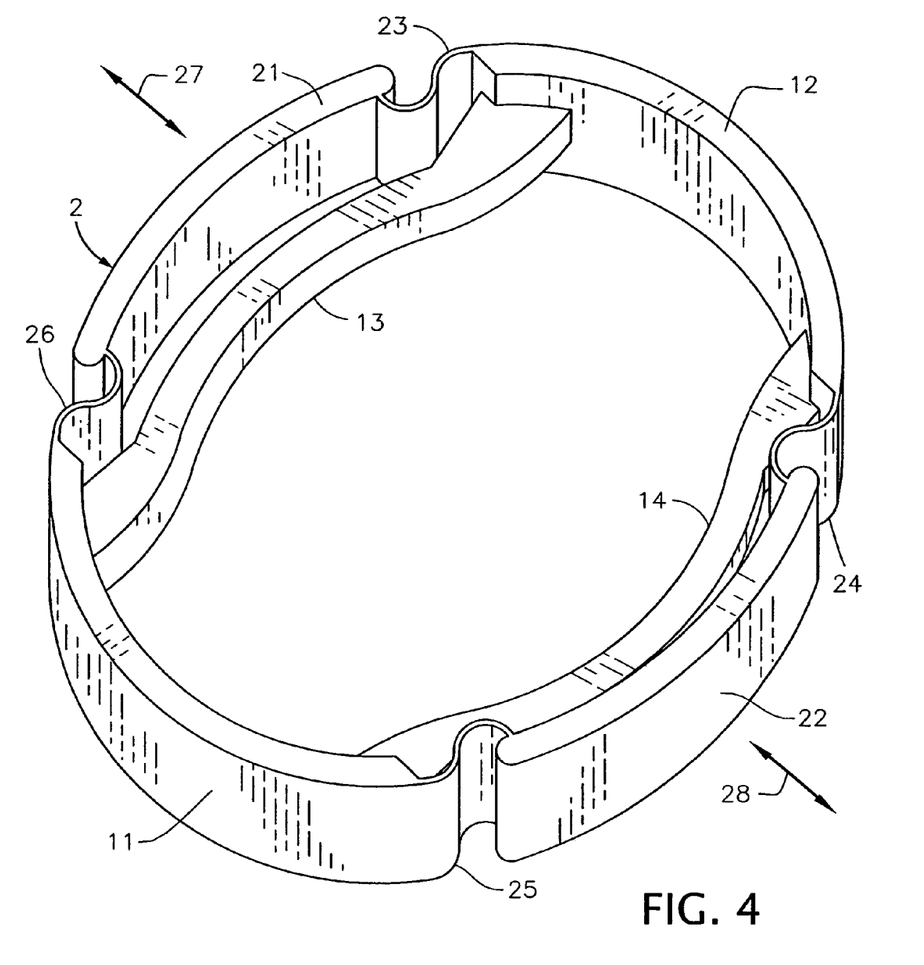
FIG. 4 is an enlarged perspective view of the perimeter ring of the second lens of the lens system of the present invention with the optic removed and in the near focused position.

FIG. 4 shows moving lens assembly 2 in the near focusing position, with some parts removed for clarity. End walls 11 and 12 are rigidly connected to one another by struts 13 and 14, so that end walls 11 and 12 cannot move relative to one another.

Pad 21 is flexibly connected by flex wall 23 to end wall 12 at one end, and flexibly connected by flex wall 26 to end wall 11 at the other end. Thus pad 21 is relatively free to move inward and outward in the directions indicated by reference numeral 27.

Similarly, pad 22 is flexibly connected by flex wall 24 to end wall 12 at one end, and flexibly connected by flex wall 25 to end wall 11 at the other end. Thus pad 22 is relatively free to move inward and outward in the directions indicated by reference numeral 28. Taken together, end walls 11 and 12 and pads 21 and 22 are arranged generally in the shape of an ellipse, where end walls 11 and 12 are at the ends of a long axis and pads 21 and 22 are at the ends of a short axis.

Figure 5:
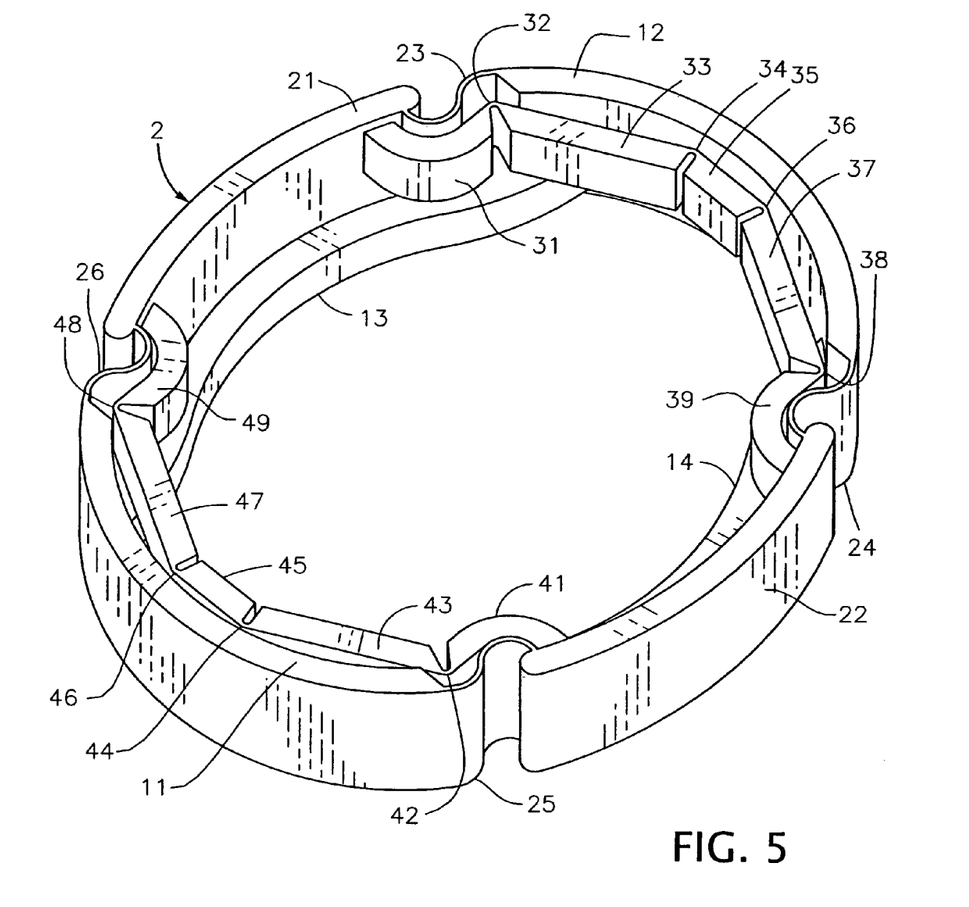
FIG. 5 is an enlarged perspective view of the perimeter ring and additional parts of the second lens of the lens system of the present invention similar to FIG. 4.

As seen in FIG. 5, moving lens assembly 2 in the near focusing position (some portions have been removed for clarity). Attached to pad 21 is bracket 31 having a curved shape passing around, without contacting, flex wall 23. Bracket 31 is raised so as to pass over, without contacting, strut 13. Link 33 is pivotably connected to bracket 31 by mean of live hinge 32. Link 33 is pivotably connected to end block 35 by means of live hinge 34. The various parts are symmetrically arranged about the long axis, so attached to pad 22 is bracket 39, having a curved shape passing around, without contacting, flex wall 24. Bracket 39 is raised so as to pass over, without contacting, strut 14. Link 37 is pivotably connected to bracket 39 by mean of a live hinge 38. Link 37 is pivotably connected to end block 35 by means of a live hinge 36. Similarly, attached to pad 22 is bracket 41, having a curved shape passing around, without contacting, flex wall 25. Bracket 41 is raised so as to pass over, without contacting, strut 14. Link 43 is pivotably connected to bracket 41 by mean of live hinge 42. Link 43 is pivotably connected to an end block 45 by means of live hinge 44. The various parts are symmetrically arranged about the long axis, so attached to pad 21 is bracket 49, having a curved shape passing around, without contacting, flex wall 26. Bracket 49 is raised so as to pass over, without contacting, strut 13. Link 47 is pivotably connected to bracket 49 by mean of live hinge 48. Link 47 is pivotably connected to end block 45 by means of live hinge 46. The term "live hinge" is known in the field of plastics as a thin belt of material, which provides a pivoting action. Each live hinge noted by reference numerals 32, 34, 36, 38, 42, 44, 46, and 48 allows rotation about an axis perpendicular to the plane of the ellipse.

Links 33, 37, 43, and 47 are positioned at a certain angle, one that amplifies movement. For example, if pads 21 and 22 are each moved outward "one unit of distance," then the links power end blocks 35 and 45 to each move inward "more than one unit of distance."

Figure 6:
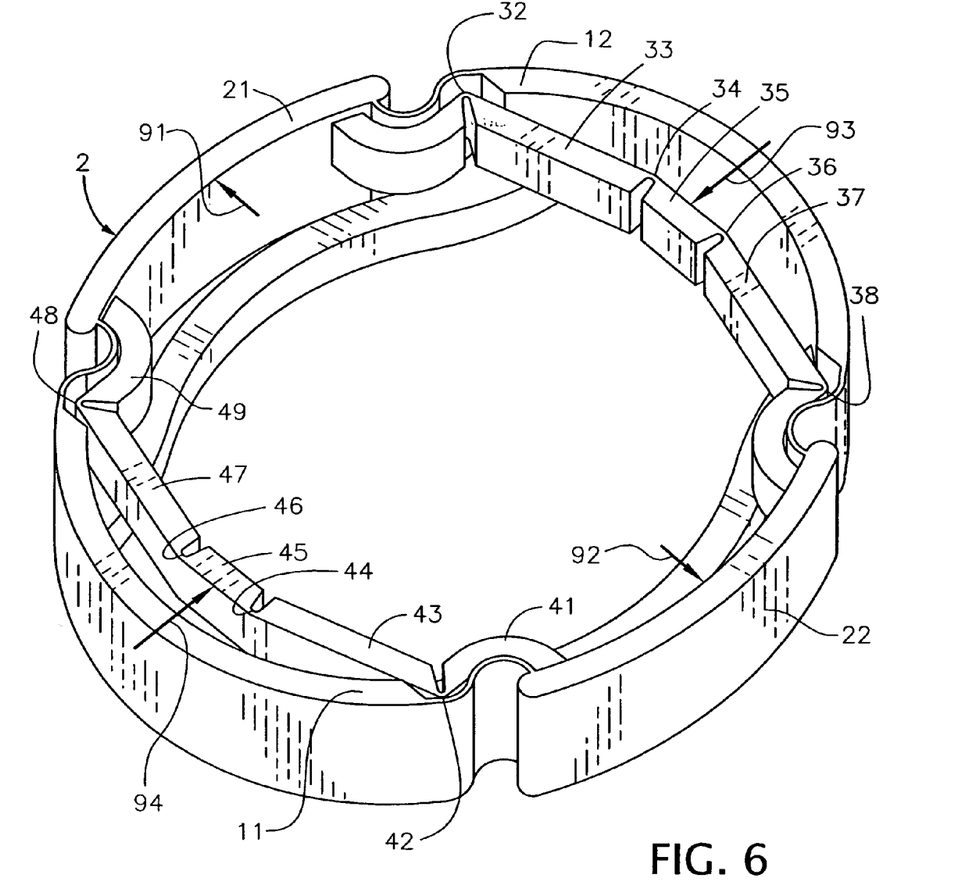
FIG. 6 is an enlarged perspective view of the perimeter ring and additional parts of the second lens of the lens system of the present invention with the optic removed and in the far focused position.

Now referring to FIG. 6, moving lens assembly 2 is shown in the far focusing position where pads 21 and 22 each have been moved outward as shown by vectors noted by reference numerals 91 and 92, while end blocks 35 and 45 each have been powered inward as shown by vectors noted by reference numerals 93 and 94. For the particular geometry of the embodiment shown, vectors 93 and 94 each have a magnitude more than twice that of vectors 91 and 92.

Figure 7:
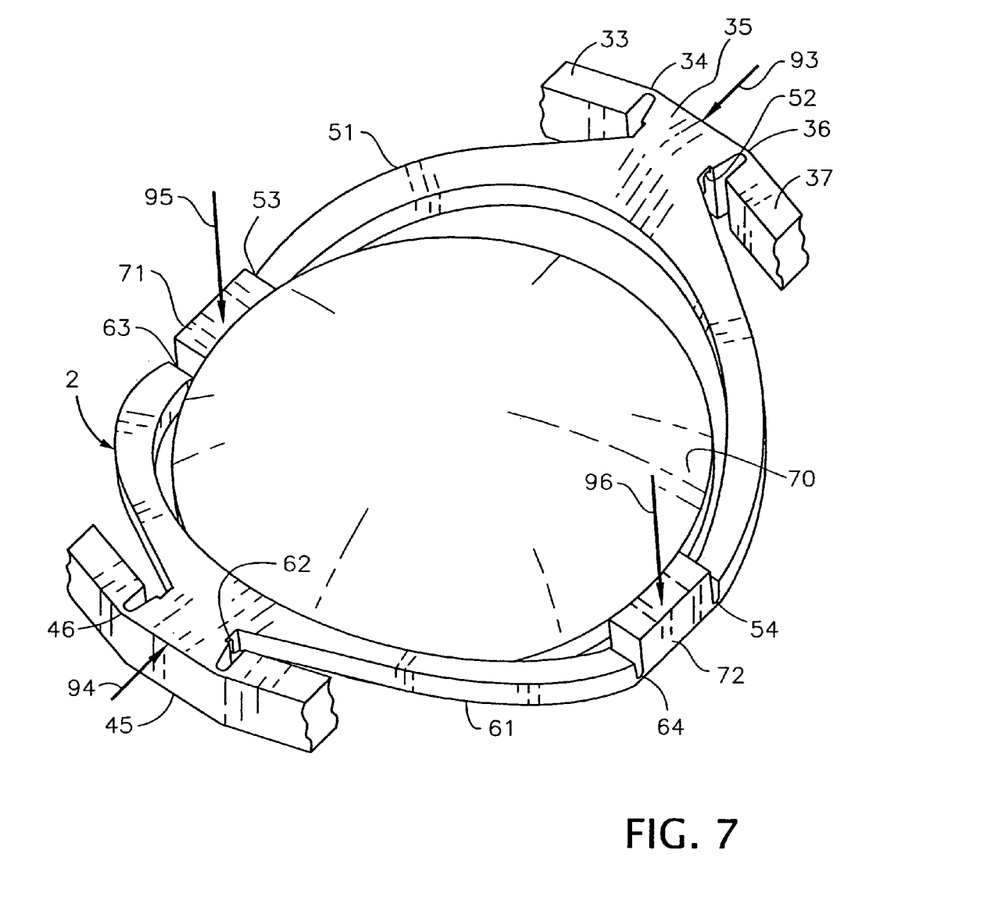
FIG. 7 is an enlarged perspective view of the perimeter ring of the optic of the lens system of the present invention in the far focused position.

FIG. 7 further discloses the construction of moving lens assembly 2 in the far focusing position, where some parts previously shown in FIG. 6 have been removed for clarity. Yoke 51 is pivotably connected to end block 35 by live hinge 52. One arm of yoke 51 is pivotably connected to lens block 71 by live hinge 53. The other arm of yoke 51 is pivotably connected to lens block 72 by live hinge 54. Yoke 61 is pivotably connected to end block 45 by live hinge 62. One arm of yoke 61 is pivotably connected to lens block 71 by live hinge 63. The other arm of yoke 61 is pivotably connected to lens block 72 by live hinge 64. Lens blocks 71 and 72 are each fixed on opposing edges of moving lens 70. Vectors noted by reference numerals 93 and 94 show the end block movements previously described. Vectors noted by reference numerals 95 and 96 show the corresponding movements of lens blocks 71 and 72, having been powered by yokes 51 and 61. Each live hinge noted by reference numerals 52, 53, 54, 62, 63, and 64 allows rotation about an axis parallel to the short axis of the ellipse.

Yokes 51 and 61 are positioned at a certain angle, one that amplifies movement. For example, if end blocks 35 and 45 are each moved "one unit of distance," then the yokes power lens blocks 71 and 72 (along with moving lens 70) to each move "more than one unit of distance." For the particular geometry of the embodiment shown, vectors 95 and 96 each have a magnitude more than twice that of vectors 93 and 94.

Thus, there is a compound action wherein the amplifying movement of links 33, 34, 43, and 44 is further multiplied by the amplifying movement of yokes 51 and 61. For the particular geometry of the embodiment shown, vectors 95 and 96 each have a magnitude about five times that of vectors 91 and 92 (shown in FIG. 6.). In other words, if pads 21 and 22 move 0.2 mm inwardly, lens 70 will move about 1.0 mm axially in this embodiment.

Figure 8:
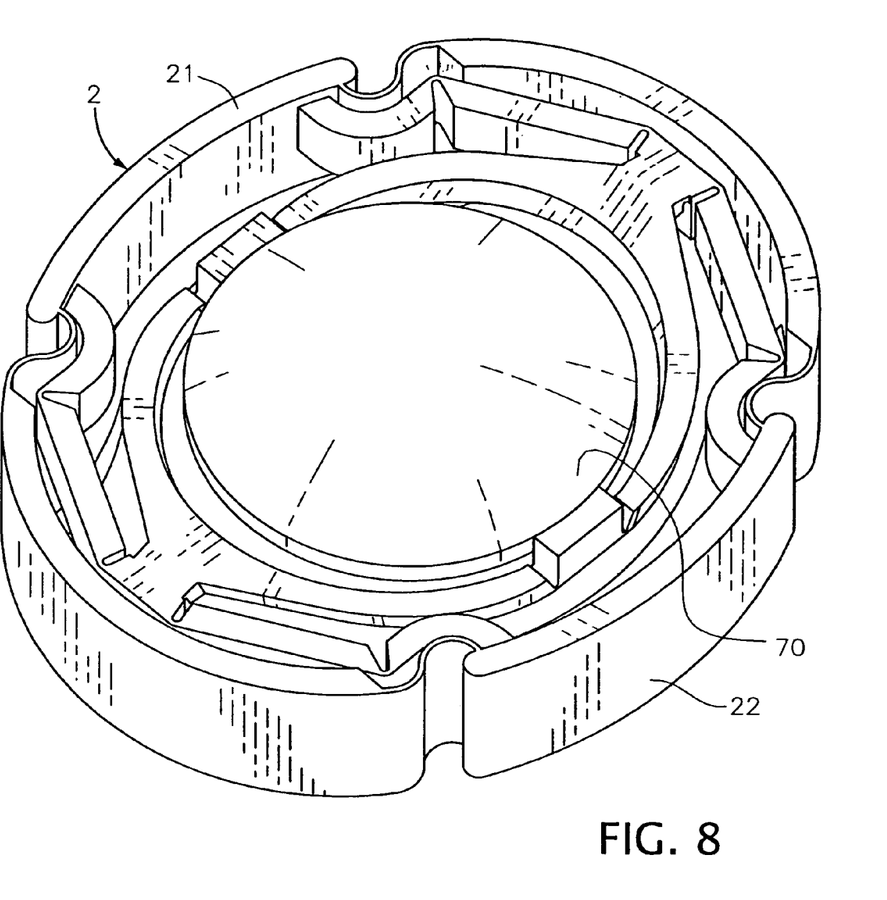
FIG. 8 is an enlarged perspective view of the lens system of the present invention in the near focused position.

Referring to FIG. 8, which shows all of the parts comprising the moving lens assembly 2 in the near focusing position. Pads 21 and 22 are located inward having powered the moving lens 70 to a high (anterior) location.

Figure 9:
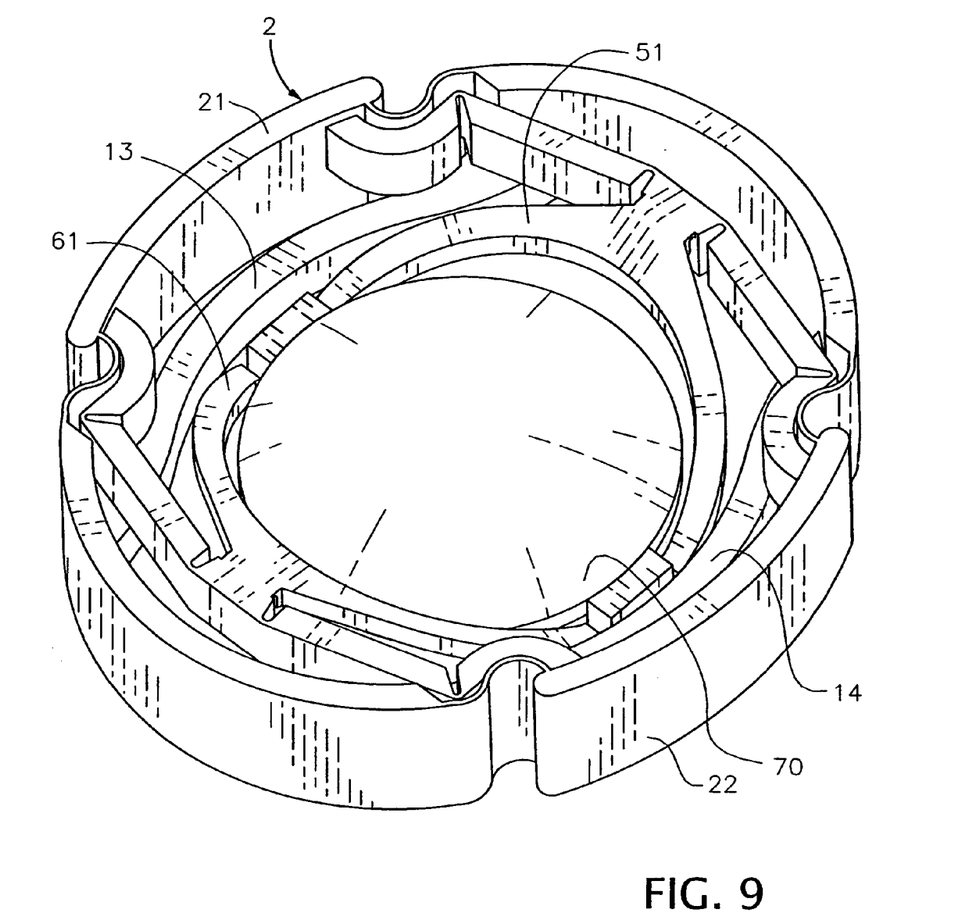
FIG. 9 is an enlarged perspective view of the lens system of the present invention in the far focused position.

FIG. 9 shows all of the parts comprising moving lens assembly 2 in the far focusing position. Pads 21 and 22 are located outward having powered the moving lens 70 to a low (posterior) location. Yokes 51 and 61 fit within, without making contact with, struts 13 and 14.

In FIGS. 1 and 3 moving lens assembly 2 is shown in cross section along the long axis of the ellipse. The long length of moving lens assembly 2 stretches the capsule C in this direction, which secures moving lens assembly 2, and which tends to slacken or reduce tension on the nearby zonules Z. This slackening of zonules insulates movement of the capsule in this area which would otherwise be caused by movement of the ciliary muscle M.

Figure 10:
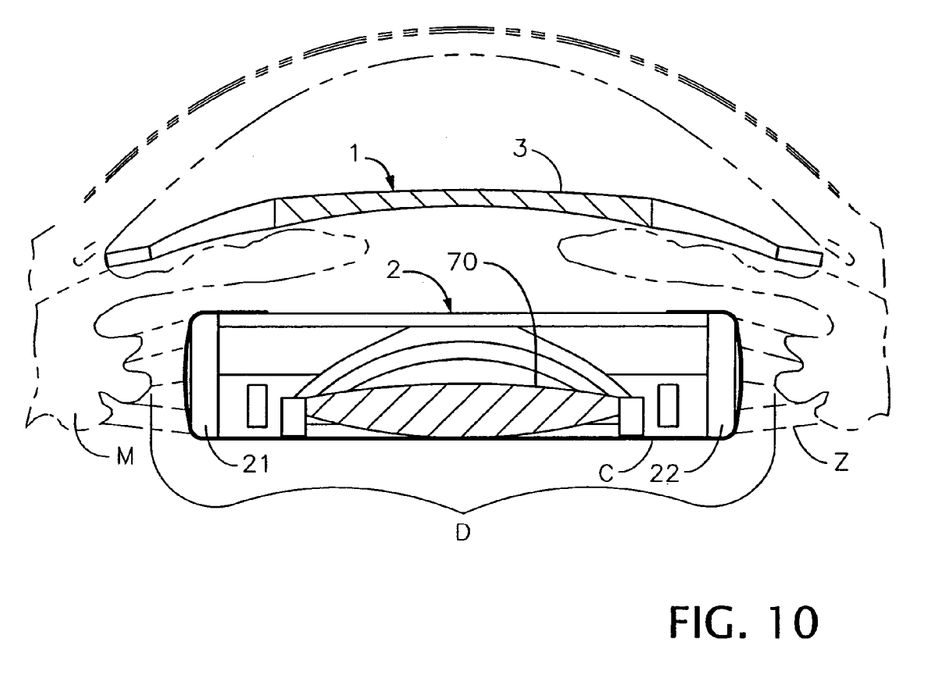
FIG. 10 is an enlarged cross-sectional view similar to FIG. 1 showing the lens system of the present invention implanted in an eye and with the second lens of the system in the far focused position.

FIG. 10 is a cross sectional side view of the present invention taken along the short axis of the ellipse, showing moving lens assembly 2 at the far focusing position, where moving lens 70 is at a posterior location, which is far from fixed lens 3. Capsule C is under circumferential tension because it is stretched along the long axis as stated before. Consequently, the sides of capsule C have a tendency to move inward. But the movement is prevented by tense zonules Z. In this view, the ciliary muscle is relaxed, which is consistent with far viewing, and a muscle span diameter D is large.

Figure 11:
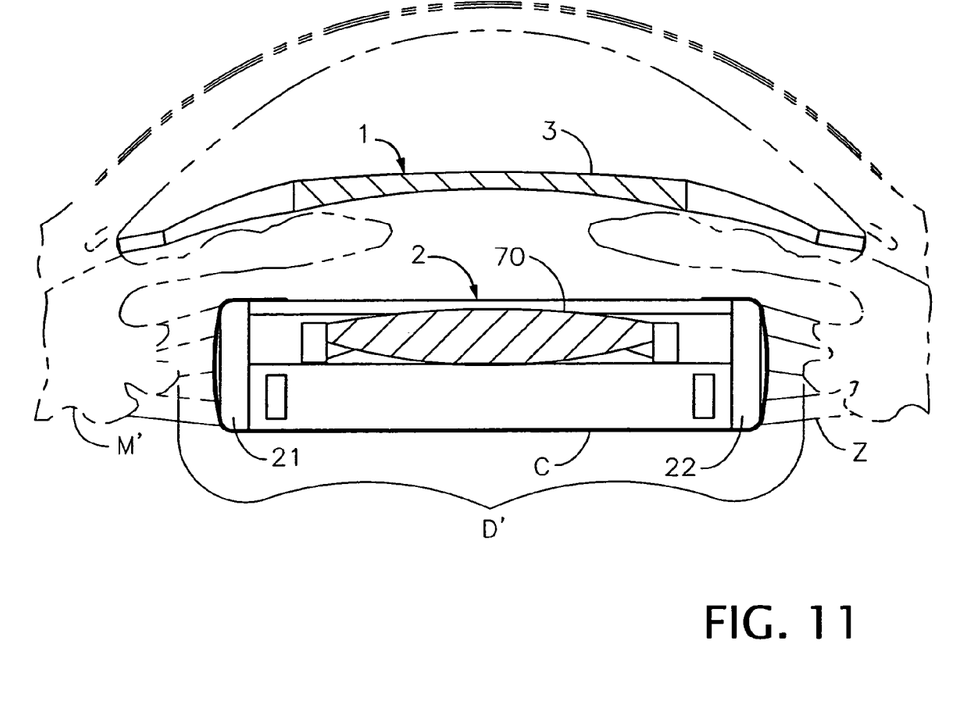
FIG. 11 is an enlarged cross-sectional view showing the lens system of the present invention implanted in an eye and with the second lens of the system in the near focused position.

Now referring to FIG. 11, the present invention is shown in cross section along the short axis of the ellipse, showing moving lens assembly 2 at the near focusing position. In this view, the ciliary muscle M' is constricted, consistent with straining for near viewing, causing a muscle span diameter D' to be smaller (than D of FIG. 10.) Therefore, the zonules Z have allowed the sides of capsule C to move closer together, consequently pushing pads 21 and 22 to move closer together, with the result that moving lens assembly 2 has assumed the near focusing position where, by the compound action previously described, moving lens 70 has moved to the anterior position, near fixed lens 3.

Also referring to FIG. 11, while the thickness of pads 21 and 22 is designed to enable inward and outward movement, the heights of pads 21 and 22 and end walls 11 and 12 are designed so as to prevent the anterior and posterior capsule membranes from moving closer to each other. This design feature improves the distance vision stability of the user.

Figure 12:
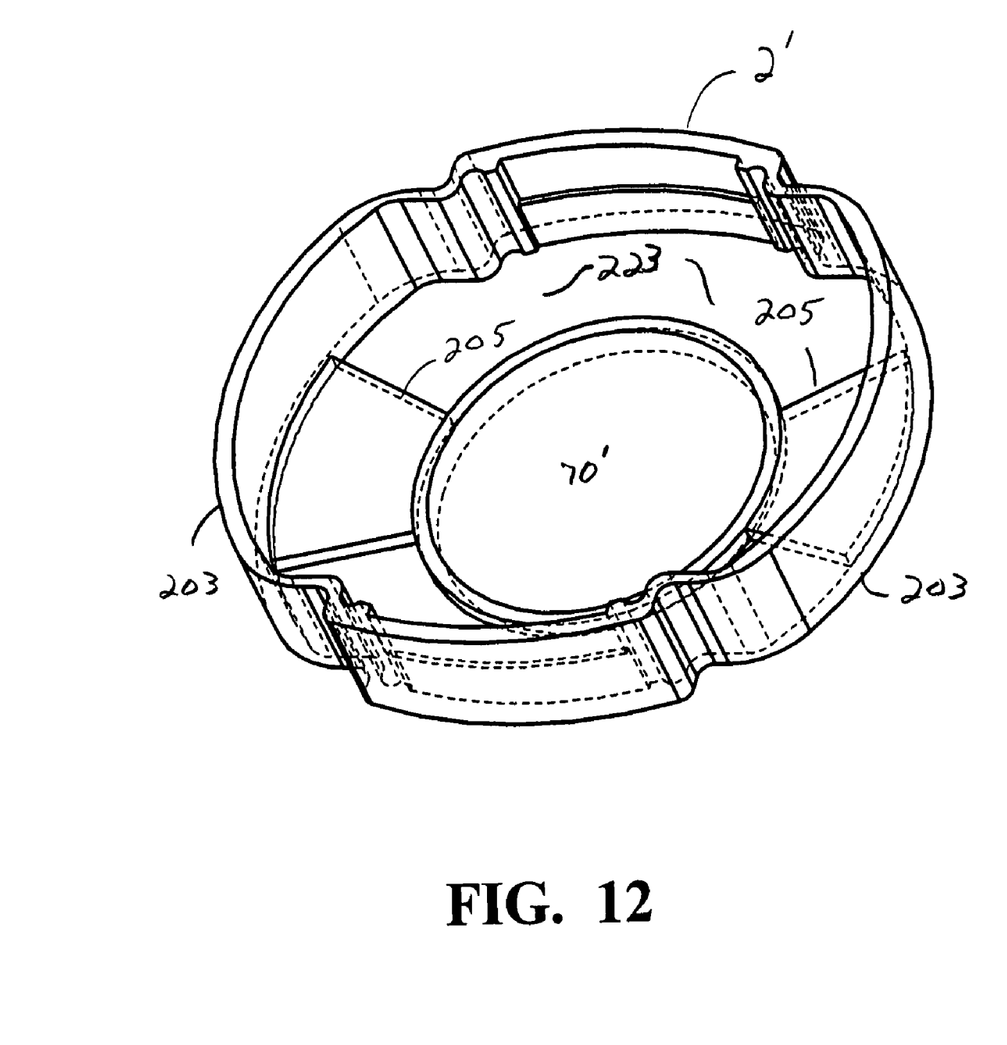
FIG. 12 is an enlarged perspective view of the optic and perimeter ring of the second lens of a second embodiment of the lens system of the present invention.
Figure 13:
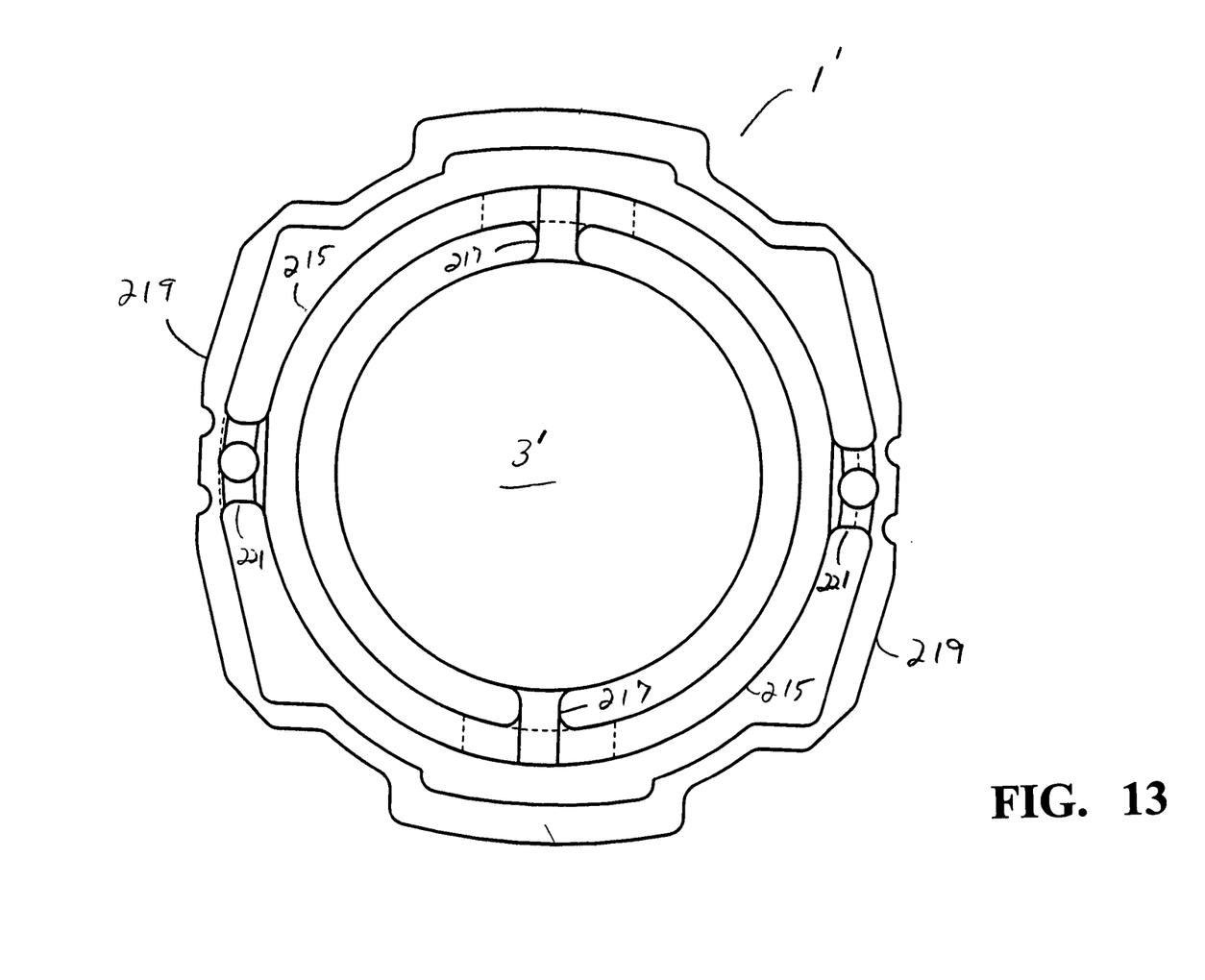
FIG. 13 is an enlarged perspective view of the optic and perimeter ring of the first lens of a second embodiment of the lens system of the present invention.

Alternatively, both lens assemblies of the lens system of the present invention may be placed in the posterior chamber, preferably in the capsular bag. As seen in FIGS. 12 and 13, lens 70' may be integrally formed with lens assembly 2' and connected to end walls 203 by haptics 205. Lens assembly 2' is generally oval in shape with open interior 223. Lens assembly 1' is formed as a separate piece from lens assembly 2' and sized slightly smaller so as to fit snugly or nest within open interior 223 of lens assembly 2'. Lens assembly 1' contains lens 3' that is attached to ring 215 by haptics 217. Ring 215 is attached to pads 219 through links 221. Links 219 transmit compressive forces on pads 203 to lens 3' through ring 215 and haptics 217 in a manner similar to that described above, causing lenses 3' and 70' to move axially relative to each other. The construction of lens assemblies 1' and 2' allow the lens system to be implanted entirely within the capsular bag.

This description is given for purposes of illustration and explanation. It will be apparent to those skilled in the relevant art that changes and modifications may be made to the invention described above without departing from its scope or spirit.

I claim:

1. An intraocular lens system, comprising:
   a) a first lens assembly;
   b) a second lens assembly having an optic;
   c) a plurality of yokes surrounding the optic and attached to the optic by a plurality of first hinges;
   d) a pair of end walls and a pair of pads, the end walls and the pads being flexibly attached and arranged generally in the shape of an ellipse surrounding the yokes;
   e) a plurality of links hingedly connected to the pair of pads; and
   f) a plurality of second hinges flexibly connecting the yokes to the links.

2. The lens system of claim 1 wherein the yokes attach to a plurality of pads, the pads being hingedly connected to the links.

3. The lens system of claim 1 wherein the end walls are connected by a plurality of struts, the struts preventing movement of the end walls relative to one another, but allowing movement of the pads relative to the end walls.

4. The lens system of claim 1 wherein the optic comprises a soft acrylic material.

5. The lens system of claim 1 wherein the second lens assembly is integrally formed as a single piece.

6. The lens system of claim 3 wherein the pads are moveable in response to movement of a ciliary muscle.

7. The lens system of claim 6 wherein inward movement of the pads in response to movement of a ciliary muscle causes axially movement of the optic.

8. The lens system of claim 7 wherein the axial movement of the optic is at least twice the inward movement of the pads.

9. The lens system of claim 8 wherein the axial movement of the optic is five times the inward movement of the pads.

10. The lens system of claim 1 wherein the first lens assembly is implanted separately from the second lens assembly.

11. The lens system of claim 1 wherein the first lens assembly is integrally formed with the second lens assembly.

* * * * *